United States Patent [19]
Koshi et al.

[11] Patent Number: 5,571,946
[45] Date of Patent: Nov. 5, 1996

[54] APPARATUS FOR AUTOMATICALLY MEASURING DUST CONCENTRATION IN FLUE GAS

[75] Inventors: Hideyuki Koshi; Hiroshi Funanokawa; Satoshi Doi; Kunihiro Kondo; Toshiyuki Umeda; Toshihiro Takahashi, all of Kawasaki-ku; Megumi Kikkawa, Hiroshima, all of Japan

[73] Assignee: NKK Corporation, Tokyo, Japan

[21] Appl. No.: 301,851

[22] Filed: Sep. 7, 1994

[30] Foreign Application Priority Data

Sep. 9, 1993 [JP] Japan .................................. 5-224423
Aug. 22, 1994 [JP] Japan .................................. 6-196432

[51] Int. Cl.$^6$ .................................................. G01N 37/00
[52] U.S. Cl. ...................... 73/28.01; 73/28.04; 73/863.25
[58] Field of Search .............................. 73/28.01, 23.33, 73/863.25, 28.04, 863.23

[56] References Cited

U.S. PATENT DOCUMENTS

| Re. 31,232 | 5/1983 | Butera | 73/28 |
|---|---|---|---|
| 4,170,127 | 10/1979 | Butera | 73/28 |
| 4,214,480 | 7/1980 | Butera | 73/421.5 A |

FOREIGN PATENT DOCUMENTS 55-97631  7/1980  Japan .
57-128830  8/1982  Japan .

OTHER PUBLICATIONS

Method of Measuring Dust Concentration in Flue Gas, pp. 647–661, JIS (Japanese Industrial Standard) Z–8808, 1992, Japan.

Primary Examiner—Hezron E. Williams
Assistant Examiner—Jay L. Politzer
Attorney, Agent, or Firm—Frishauf, Holtz, Goodman, Langer & Chick

[57] ABSTRACT

An apparatus for automatically measuring dust concentration in flue gas includes (a) a sampling unit for sampling dust in flue gas; (b) a measuring unit for measuring a gas flow of the flue gas; and (c) a feeding and weighing unit for feeding and weighing a filter paper for filtering the sampled gas, the feeding and weighing unit including (i) a filter paper cassette for storing the filter paper, (ii) a filter paper stocker for storing a plurality of the filter paper cassettes, (iii) a cassette pusher unit for pushing a filter paper cassette out of the filter paper stocker, (iv) a filter paper ascending unit for raising the filter paper, (v) a filter paper drier for drying the filter paper, (vi) a filter paper transfer arm for transferring the filter paper between the filter paper cassette, the filter paper ascending unit and the filter paper drier, (vii) a vibration-free balance for balancing the filter paper, and (viii) a hot air generation unit. A controlling unit is provided for transmitting data among the dust sampling unit, the measuring unit, and the feeding and weighing unit and for controlling a sequence of operations thereof.

15 Claims, 10 Drawing Sheets

FLUE GAS

APPARATUS FOR AUTOMATICALLY MEASURING DUST CONCENTRATION IN FLUE GAS

BACKGROUND OF THE INVENTION

1. Field of the Invention

The present invention relates to an apparatus for automatically measuring dust concentration in flue gas discharged from a heating furnace, boiler, dust collector, or the like.

2. Description of the Related Art

The Air Pollution Control Act requires that dust generating facilities such as heating furnaces and boilers have a periodic measurement of dust concentration in flue gas. The dust concentration in flue gas discharged from the dust collectors is also regulated by regional pollution prevention agreements or the like, and the measurement of the dust concentration is also required by such agreements.

An example of conventional apparatus for automatically measuring dust concentration in flue gas is given in FIG. 13 which is employed in JIS Z-8808. The apparatus comprises means for collecting dust (I), means for sucking gas (II), and means for measuring a sucked gas flow rate (III).

The dust collecting means (I) comprises a dust collector 41 which contains a filter paper 6, a Venturi tube 42, a temperature detector 43 for measuring the temperature of flue gas, and a pitot tube 9 for determining the flow rate of flue gas. Those devices are protected by a protective tube 44, and the protective tube 44 is inserted into a measuring hole 2 on a factory gas duct 1.

The gas suction means (II) comprises a conduit 45 for sucking the collected gas, a conduit 46 for pressure transmission, a pressure gauge 47, a suction pump 14, a surge motor 48, a sucked gas flow rate regulator valve 49, a flow rate controller 50, an $SO_2$ absorption bottle 12, and a mist removal bottle 13.

The gas flow rate measuring means (III) comprises a thermometer 51, a manometer 52, and a wet gas meter 15. The means further needs a drier and a desiccator for drying the filter paper and a balance for weighing the filter paper at the laboratory (IV), though these devices are not shown.

As illustrated in FIG. 13, the measurement specified in JIS Z-8808 is carried out by mounting the filter paper 6 in the dust collector 41 facing the flow direction of flue gas, by sucking the flue gas collected by the suction pump 14 at an equal flow rate to that in the pitot tube 9 of the dust collection means (I), by taking the filter paper 6 out from the dust collector 41, by transferring the filter paper 6 to the laboratory (IV), by drying the filter paper 6 in a drier followed by drying it in a desiccator, and by determining the weight of dust attached on the filter paper 6 using a balance. However, this type of measuring method is troublesome because it requires replacing the filter paper 6 and drying it, which makes the automatic measurement difficult.

There are several already developed methods of automatic measurement of dust concentration in flue gas, which include a light scattering method, a light permeation method, a β ray absorption method, a capacitance method and so on.

Unexamined Japanese Patent Publication No. 57-128830 discloses an automatic dust concentration automatic measuring technology using the β ray method. FIG. 14 illustrates a scheme of the prior art dust concentration measuring apparatus disclosed in the patent publication.

The dust concentration measuring apparatus has the following characteristics.

Reference number 101 denotes a gas sampling tube for collecting sample gas, 102 is a heating tube for introducing the sample gas, 103 is a dust collector for collecting dust in the sampled gas, 104 is a suction piping, 105 is a valve for adjusting the suction gas flow rate, 106 is a suction pump, 107 is a gas meter which generates pulses corresponding to the mass signals of the sucked sample gas, 108 is a coiled filter paper tape, 109 is a motor reel for coiling and uncoiling of the filter paper, 110 is a feed roller for feeding the filter paper back and forth, 111 is a pinch roller for securing a smooth transfer of the filter paper, 112 is a radio isotope generator which emits β rays, 113 is an isotope detector, 114 is a mass calculator for computing the dust mass from the quantity of the β rays permeating through the paper, 115 is a flow rate calculator for computing the flow rate from the received flow rate pulse signals sent from the gas meter 107, 116 is a concentration calculator for determining the dust concentration from the output of the mass calculator 114 and the output of the flow rate calculator 115, 117 is a sequence control circuit for controlling the action of the dust concentration meter. With these devices, the dust concentration meter is structured. Nevertheless, this type of apparatus is only used for measuring the quantity of a specific element. For this reason, this type of apparatus has a problem of poor accuracy in the measurement of concentration of dust containing various kinds of elements.

An example of a weighing method of the prior art automatic dust concentration measurement technology is disclosed in Unexamined Japanese Utility Model Publication No. 55-97631.

The disclosed technology is a type of automatic falling dust sampling and measuring unit, which automatically weighs the falling dust and which transmits the data after classifying the data according to the direction of gas flow and the amount of time. This apparatus comprises a collection funnel which collects the falling dust, a rotary table which supports more than one sample bottle, a driving unit which intermittently drives the rotary table to position each of the sample bottles, in turn, at the dust receiving point under the dust collection funnel, a weighing device which weighs the dust in the sample bottle, a circuit which classifies the collected data for each direction of gas flow and amount of time. This apparatus, however, does not include a means for providing correction of the data for the moisture content in the flue gas. For this reason, the accuracy of measurement with this apparatus is poor.

SUMMARY OF THE INVENTION

The object of the present invention is to provide an apparatus for automatically and quickly measuring dust concentration in flue gas, which is compact in construction and is lightweight.

To achieve this object, the present invention provides an apparatus for measuring dust concentration in flue gas, which comprises:

(a) sampling means for sampling dust in flue gas;
(b) measuring means for measuring a gas flow rate when the flue gas is sucked;
(c) feeding and weighing means for feeding and weighing a filter paper for filtering the sampled gas, said feeding and weighing means comprising a filter paper cassette for storing the filter paper, a filter paper stocker for storing a plurality of the filter cassettes, a cassette pusher unit for pushing the filter paper cassette out of the filter paper stocker, a filter paper ascending unit, a filter paper drier for drying the filter paper, a filter paper transfer arm for transferring the filter paper, a vibration-free balance for balancing the filter paper and a hot air generation unit; and (d) controlling means for transmitting data among said sampling means, said measuring means, and said feeding and weighing means, and controlling the sequence of operations.

Furthermore, the present invention provides an apparatus for measuring dust concentration in flue gas, which is characterized in that in addition to the above-mentioned apparatus, the filter paper ascending unit, the drier, the filter paper transfer arm, and the vibration-free balance are located at a periphery of a rotatable turntable.

DESCRIPTION OF THE PREFERRED EMBODIMENT

Figure 1:
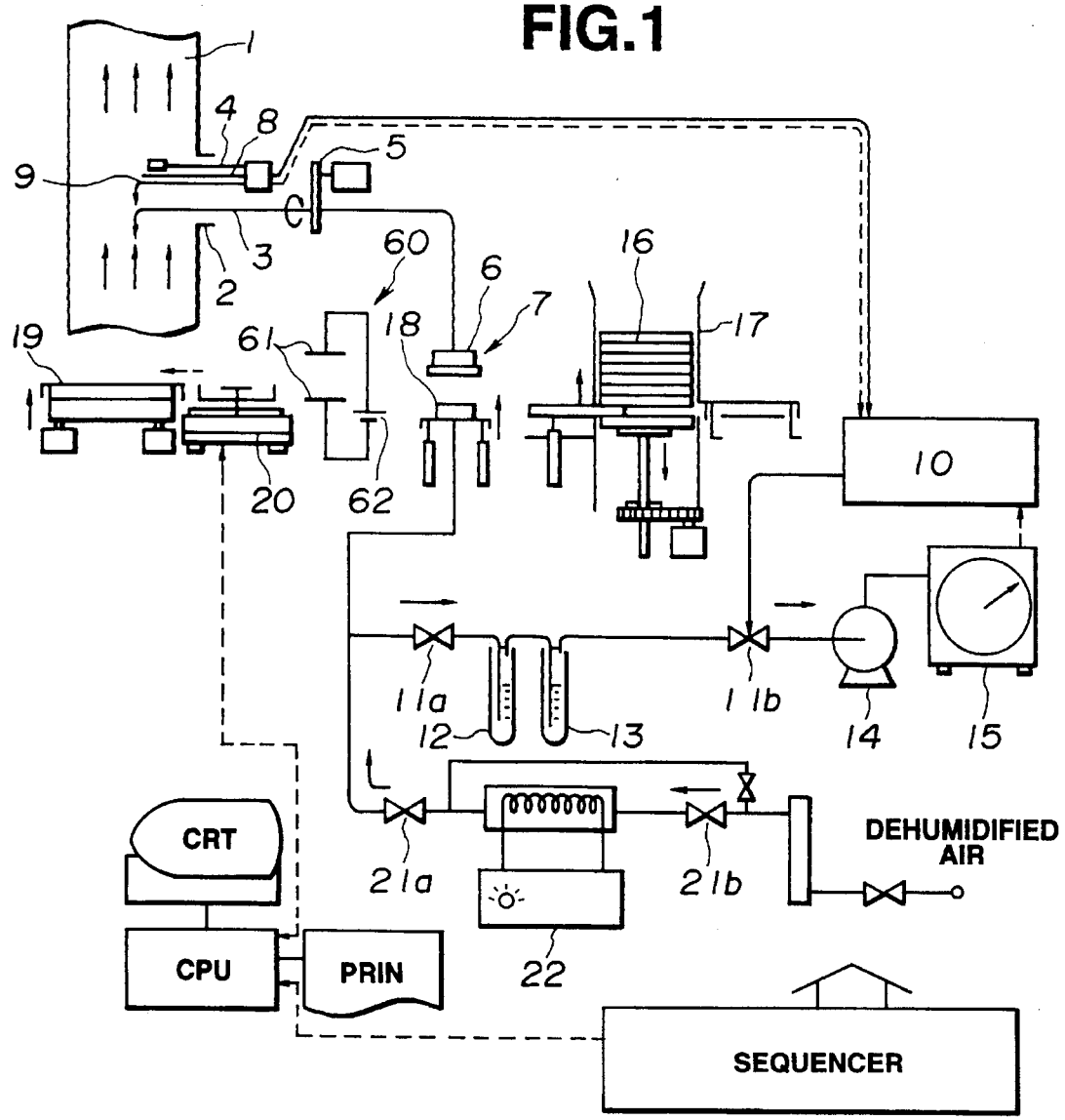
FIG. 1 is a schematic view illustrating an apparatus for automatically measuring dust concentration in flue gas, according to the present invention.

The present invention comprises means for sampling dust, means for measuring a sucked gas flow rate, means for feeding and weighing filter paper, and means for controlling the data of said sampling means, said measuring means, said feeding and weighing means, and controlling the sequence of operations thereof. Accordingly, the invention enables the automatic measurement of dust concentration in flue gas according to a method conforming to JIS-Z-8808 (weighing method). Furthermore, the apparatus of the present invention apparatus also enables the transferring and weighing of filter paper in advance and the use of remote control.

Furthermore, since the present invention comprises a turntable system wherein the sampling means, the measuring means, the feeding and weighing means, and the controlling means are placed on the periphery of a turntable, the present invention has an advantage of simultaneous implementation of the dust sampling with other activities.

As for the effects of the present invention, these include use of a vibration-free balance to enable weighing to be performed with precision even under a vibratory environment, the elimination of extra drying time due to the use of a hot air drier and a moisture meter, the prevention of dust adhering to a sampling tube due to a reversing unit which places the sampling tube under a negative pressure during a non-sampling time, the assurance of an accurate measurement due to elimination of dust remaining from a previous measurement, the compactness of the apparatus due to use of a filter paper cassette, a filter paper transfer arm and a hot air drier which are exclusively used for the filter paper, and the easy transport of the apparatus due to the filter cassette, filter transfer arm and hot air drier, thus enabling a single apparatus to be applied to more than one gas duct for gas concentration measurement.

In addition, the dust sampling tube introduces the flue gas to the filter paper by sucking the flue gas through a suction opening with an equal flow rate suction. When the flue gas flows in the form of a laminar flow, the gas flow rate becomes zero in the inner wall of the gas sampling tube and thus, the dust easily adheres to the inner wall and piles up there. This adhesion and the piling of the dust are with the sampling tube closed. To avoid the dust adhesion, a sectional area of the sampling tube has Reynolds number of 2000 or more. This arrangement of the sectional area of the sampling tube makes the gas flow form a turbulent flow and the dust adhesion can be prevented in advance.

The Reynolds number $R_r$ of the gas sampling tube is represented by the following equation:

$$R_r = R \times V \times \rho / \eta \ldots \quad (1)$$

where
R is the inner diameter of the tube×½ (=radius),
V is the average flow rate,
ρ is the density of the fluid, and
η is the viscosity of the liquid.

When the flow rate of the flue gas which is to be measured is supposed to be 4 to 7 m/sec., the flow rate of the flue gas which is introduced through a suction inlet varies in the mentioned range of 4 to 7 m/sec. since the flue gas is sucked at an equal suction flow rate. On the condition that the density ρ of the flue gas is 1.0 kg/m$_3$ (nearly equal to the density of air), and that the viscosity η of the flue gas is $26 \times 10^{-6}$ N·S/m$^2$ (nearly equal to the viscosity of air under 1 atmosphere at 200° C.), $R_r \geq 2000$ is obtained.

Thus, the dust adhesion to the inner wall of the sampling tube is prevented in advance.

The dust sampling tube is placed in the flow route of the flue gas containing gas dust. The sampling tube sucks the flue gas through a suction opening with an equal suction flow rate and introduces the flue gas to the filter paper. At a predetermined location of a periphery of the sampling tube, a projection is placed and a vibration ring, which is rotatable and rotates by dust laden air, is set in the sampling tube to vibrate the sampling tube. This vibration prevents the dust from adhering and piling up onto the inner wall of the sampling tube in advance.

When the dust of the flue gas coming from the gas duct is charged with electricity by means of an electric dust collector, the filter paper is electrified due to the adhesion of the dust with the electricity. The electrified filter paper is discharged by a means for discharging electricity. This discharging prevents an error from arising, due to static electricity, with respect to the results of measurement by the vibration-free balance.

EXAMPLE

With reference to the drawings, an example of the present invention will now be described. FIG. 1 is a view illustrating a total structure of an apparatus for automatically measuring dust concentration in flue gas according to the present invention. The solid lines indicate conduits of the flue gas and other gases such as air, and the broken lines indicate electric signal lines.

As shown in FIG. 1, an apparatus for automatically measuring dust concentration in flue gas comprises means for sampling dust, means for measuring a sucked gas flow rate, means for feeding and weighing a filter paper, and means for controlling measurement.

First, the dust sampling means is inserted into a measuring hole 2 in a gas duct 1. The dust sampling means comprises a dust sampling tube 3 which faces the direction of flue gas flow while the flue gas is being measured, a reversing unit 5 which is equipped with a low speed motor, for example, and which rotates a sampling opening of the dust sampling tube 3 so that the sampling tube faces in a direction opposite to the direction of flue gas flow, as marked by arrows in the figure when the flue gas is not measured, and a filter paper holder 7 which holds a filter paper 6 to collect dust from the flue gas.

The sucked gas flow rate measuring means comprises a thermocouple 8 which is inserted into the measuring hole 2 and which determines the flue gas temperature, a moisture meter 4 which determines moisture content of the flue gas, a pitot tube 9 which measures the gas flow rate while the flue gas is collected, a flow rate suction unit 10 which sucks the collected gas at an equal flow rate with that of the flue gas, switch valves 11a and 11b which switch the collected gas, an $SO_2$ absorption bottle 12 which absorbs $SO_2$ gas in the collected gas, a mist removal bottle 13 which removes mist from the collected gas, a gas suction pump 14, a gas meter 15 which determines the quantity of the sucked gas, and gas conduits.

Figure 3:
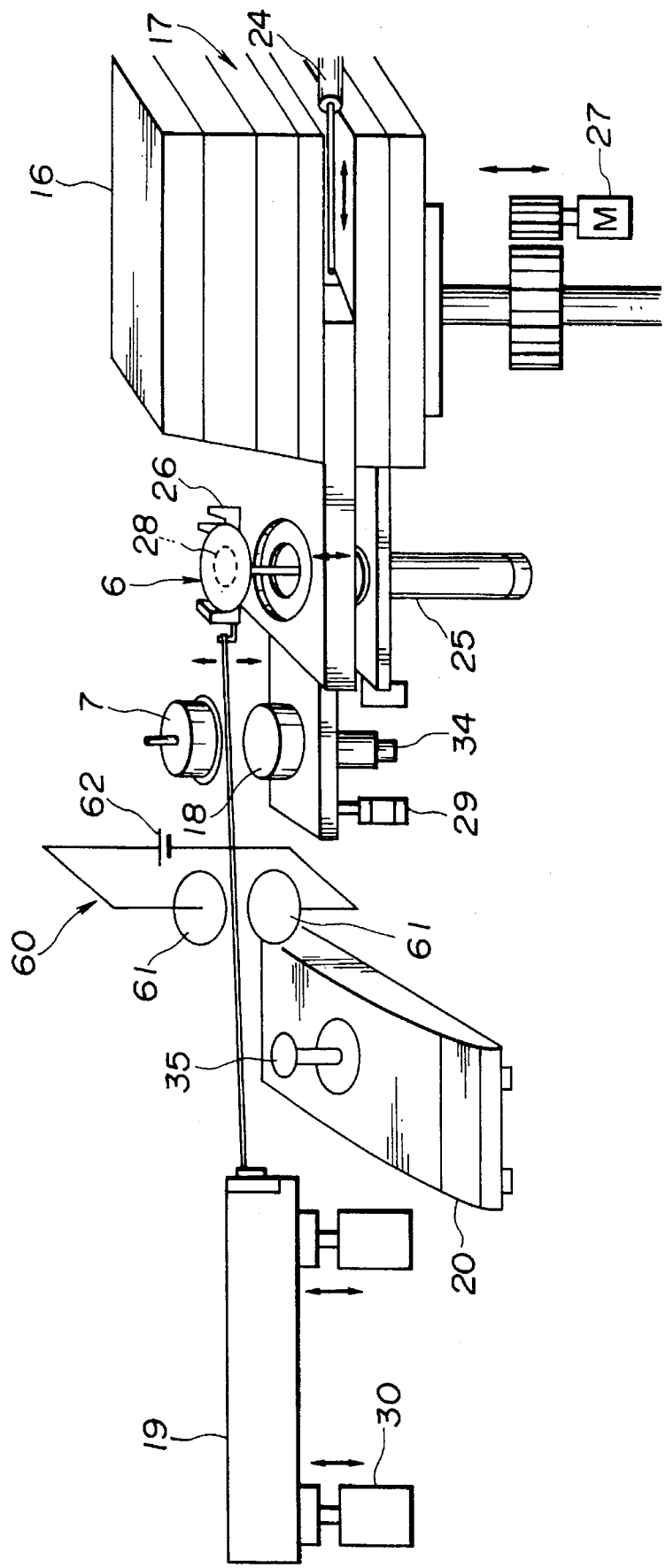
FIG. 3 illustrates in detail, means for feeding and weighing filter paper, according to the present invention.

As shown in FIGS. 1 and 3, the filter paper feeding and weighing means comprises filter paper cassettes 16 which store the filter papers 6, a filter paper stocker 17 which stores more than one cassette 16, a cassette pusher unit 24 which pushes out each of the cassettes 16 from the filter paper stocker 17, a filter paper ascending unit 25, a filter paper dryer 18 which dries the filter paper 6, a filter paper transfer arm 19 which transfers the filter paper 6, a vibration-free balance 20 which weighs the filter paper 6, switch valves 21a and 21b which switch the sampled gas to and from hot air, a hot air generator 22, and a piping which supplies dehumidified air. Further, the dust contained in the flue gas which has passed through an electrical dust collector is usually charged with negative electricity. Thus, since the filter paper which has collected the dust is also charged with negative electricity, the negative electricity of the filter paper is discharged by having the filter paper pass between electrodes 61 of a means for discharging electricity 60. The electrodes 61 are connected to a direct current power source.

Lastly, the measurement controlling means comprises, as indicated by dashed lines in the figure, a sequencer which controls transmission of characteristics of the flue gas flowing between the dust sampling means and the sucked gas flow rate measuring means and controls transfer and weighing of the filter paper in the filter paper feeding and weighing means by means of electric signals, and a CPU, a CRT, and a PRIN (printer).

Figure 2A:
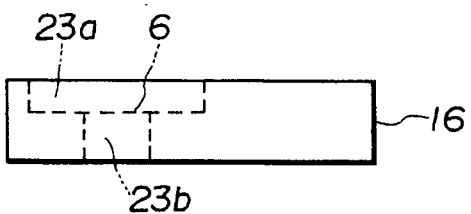
FIG. 2(A) is a side view of a filter paper cassette according to the present invention.
Figure 2B:
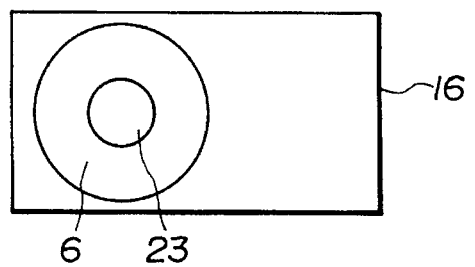
FIG. 2(B) is a plan view of the filter paper cassette of FIG. 2(A)
Figure 4:
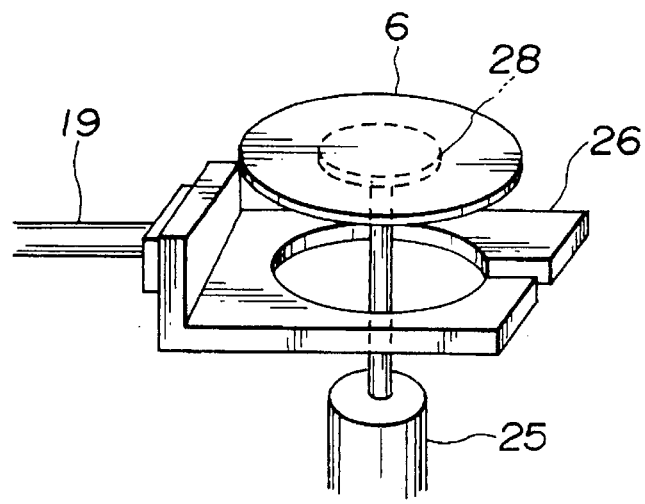
FIG. 4 is a perspective view of means for holding filter paper in the present invention.

FIG. 2(A) shows a side view of the filter paper cassette and FIG. 2(B) a plan view of the filter paper cassette, according to the present invention. FIG. 3 illustrates means for feeding and weighing the filter paper. FIG. 4 shows the filter paper holding means of the present invention.

As seen in FIGS. 2(A) and 2(B), a recess 23a is provided at a top of the filter paper cassette 16 to receive the filter paper 6. The filter paper cassette 16 stores the filter paper 6 of circular shape, as specified in JIS, on a flat plate 28 of a filter paper ascending unit 25, in recess 23a. At a bottom of the filter paper cassette 16, there is provided a through-hole 23b which is capable of lifting the filter paper using flat plate 28.

FIG. 3 shows cassette pusher unit 24 which pushes out each of the filter paper cassettes 16 horizontally from filter paper stocker 17 by means of an air cylinder, filter paper ascending unit 25 which raises the filter paper 6 on flat plate 28, a filter paper holding unit 26 which holds the filter paper 6, a filter paper stocker driving unit 27 provided with a limit switch, and an ascending and descending cylinder 29 which raises or lowers filter paper drier 18.

To carry out the dust measurement, a limit switch of the filter paper stocker driving unit 27 is set to a position where the lowest one of the filter cassettes 16 comes to a pushing point of the cassette pusher unit 24, and the filter paper cassette is moved to the set position. Then, the filter paper cassette 16 is pushed out to the full stroke of the air cylinder of the cassette pusher unit 24 until the filter paper cassette 16 is positioned just above the flat plate 28 of the filter paper pusher unit 25.

Next, as shown in FIG. 3 and FIG. 4, the filter paper 6 on the flat plate 28 is lifted to a full stroke of an air cylinder of the filter paper ascending unit 25. The filter paper 6 is thereby removed from and raised above from the filter paper cassette 16. The filter paper transfer arm 19 is then moved so that the raised filter paper 6 is held by the filter paper holder unit 26 on the filter paper transfer arm 19 for transfer to the filter paper drier 18. The positioning of the filter paper drier 18 is set by the limit switch.

The position of stopping an air cylinder of the filter paper transfer arm 19 is set to correspond to the positioning of the filter paper ascending unit 25 at the point of full stroke. As seen in FIG. 3, the filter paper transfer arm 19 is provided with an ascending and descending air cylinder 30.

Figure 5:
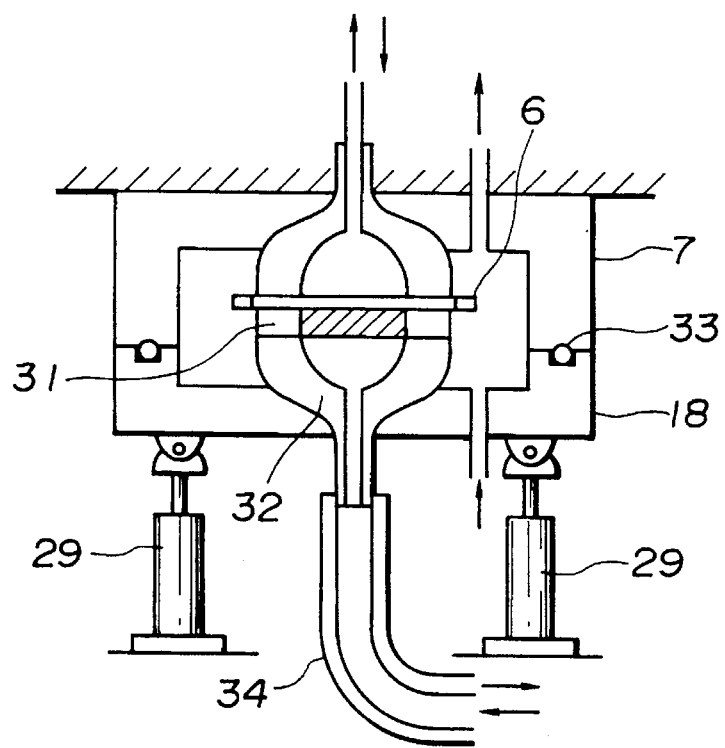
FIG. 5 illustrates how to measure dust by a combination of a filter paper holder and a filter paper drier in the present invention.
Figure 6:
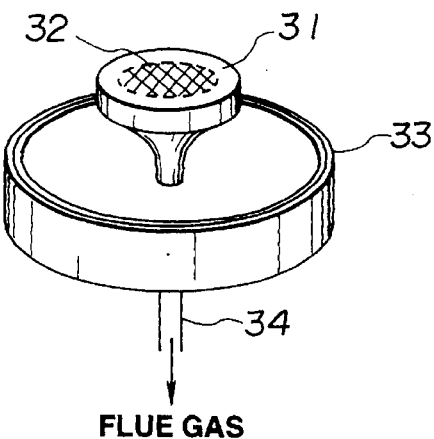
FIG. 6 is a perspective view of a head of the filter paper drier in the present invention.

FIG. 5 illustrates how to measure dust by a combination of the filter paper holder 7 and the filter paper drier 18, and FIG. 6 gives a detailed illustration of a head of the filter paper drier 18.

FIG. 5 and FIG. 6 describe a filter paper holding seat 31, a honeycomb suction mesh 32 to prevent separation of the filter paper, an O-ring seal 33 made of a heat-resistant silicone rubber to seal hot air and dehumidified air, and a conduit 34 introducing the flue gas, the hot air, and the dehumidified air.

As illustrated in FIG. 5 and FIG. 6, the hot air and the dehumidified air flow upward from the bottom of the filter paper drier 18 during the filter paper drying stage, and flow downward as illustrated by the arrow in FIG. 6 during the measuring stage. The filter paper drier 18 ascends and descends by means of the ascending and descending air cylinders 29 located at the bottom of the filter paper drier 18.

Figure 7A:
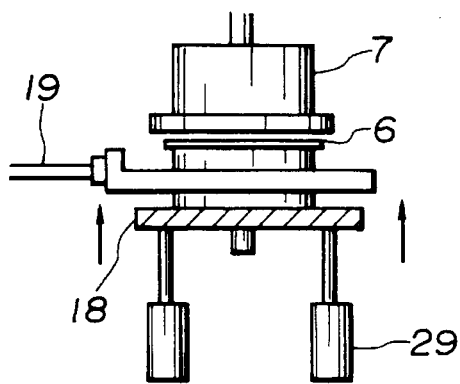
FIG. 7(A) shows a dust measuring state in the present invention.
Figure 7B:
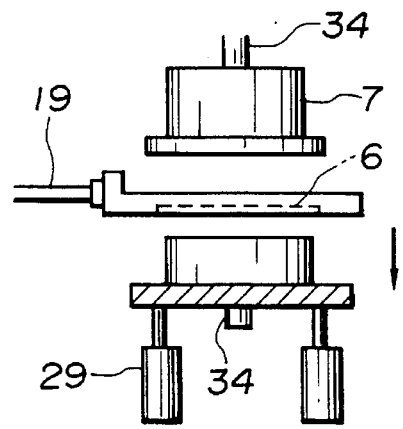
FIG. 7(B) shows a filter paper taken up state in the present invention.

FIGS. 7(A) and 7(B) show a combined state of the filter paper holder 7 and a head of the filter paper drier 18 under the dust measuring stage, and the filter paper taken up state, respectively. During the dust measuring stage which is illustrated in FIG. 7(A), the filter paper drier 18 ascends by means of the ascending and descending cylinder 29, and takes up the filter paper 6 from the filter paper holding unit 26 to sandwich the filter paper between the filter paper holder 7 and the filter paper drier 18 for measuring. When the sampling is completed, the filter paper drier 18 descends by means of the ascending and descending cylinder 29 to leave the filter paper 6 on the filter paper transfer arm 19 as shown in FIG. 7(B).

By applying gas suction during the descending action of the lower part of the filter paper holder 7 after the completion of the measurement, the filter paper 6 is easily taken out from the top of the filter paper drier 18.

Figure 8:
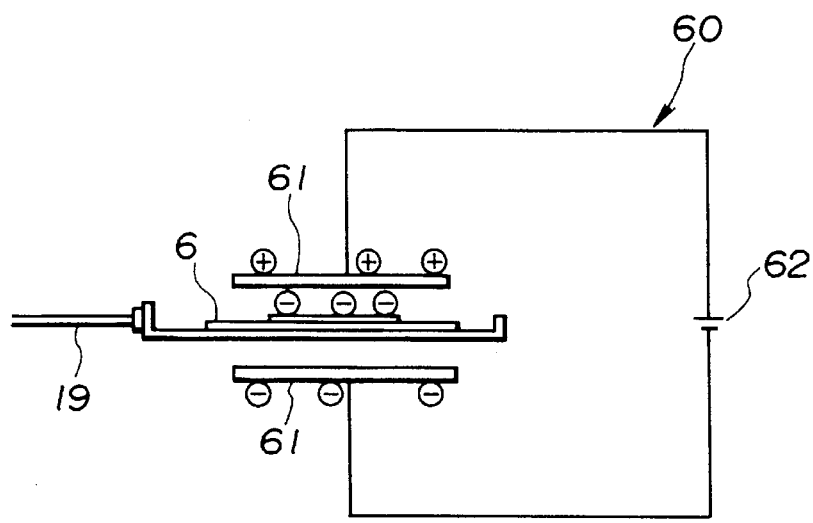
FIG. 8 is an explanatory view showing a method for discharging electricity from the dust which is charged with electricity.

FIG. 8 shows a state where a means for discharging electricity 60 discharges the filter paper which is electrified. Electrodes 61 are placed at a predetermined interval and are connected to a direct current power source 62. The dust collected by the filter paper 6 is charged with negative electricity. In this electrified state of the filter paper 6, static electricity provides an error in the results of the measurement of the filter paper by the vibration-free balance 20. To remove this error, the negative electricity of the filter paper is discharged by having the filter paper pass between the electrodes 61 of the electricity discharge means 60. For the discharge, the side of the filter paper to which the dust with the negative electricity adheres is made to face the electrode 61 charged with positive electricity.

The controlling means comprises a sequencer, CPU, CRT and PRIN (printer).

The sequencer controls the action of each of the units by using a time schedule and a limit switch for actuating the motor of the reversing unit 5 in the sampling means, for actuating the gas suction pump 14 and the switch valves 11a and 11b in the flow rate measuring means, for actuating the cylinder on the filter paper transfer arm 19, the cassette pusher unit 24, the filter paper ascending unit 25, the ascending and descending cylinder 29 and the air cylinders 30, for actuating a motor of a rotary unit 37 of a turntable 36, and for actuating the filter paper drier 18 or a hot plate 38. The CPU enters and arbitrarily sets a dust measuring initiation time, a number of dust measuring cycles, a gas suction time, and a filter paper drying time and receives measured data (gas flow rate, weight of filter paper, moisture content, and gas temperature) to calculate the dust concentration. The CRT displays data on a screen for input and confirmation of these data. The PRIN prints the measured data.

Referring to the drawings of figures, how the measurement is carried by using the apparatus of the present invention will now be explained.

Preparation of Filter Paper

The filter papers 6 are prepared as follows. The filter papers 6 are manually placed in the recess 23a of the filter paper cassette 16 sheet by sheet. As shown in FIG. 1, the cassettes 16 are piled in the filter paper stocker 17.

5 to 10 of filter paper cassettes 16 are preferably put in the filter paper stocker 17 in advance, and then, a single sheet of filter paper is taken out at every measuring cycle by means of an ascending and descending motor 27. Such operation prevents damage of the filter paper 6 and makes handling of the filter paper easy.

Feed of Filter Paper

The filter papers are fed as described below.

(1) As illustrated in FIG. 3, the limit switch of the filter paper stocker driving unit 27 is automatically set to position the lowest filter paper cassette 16 at the push out point of the cassette pusher unit 24.

(2) The lowest filter paper cassette 16 is pushed out by the air cylinder of the cassette pusher unit 24 to its full stroke to locate the cassette 16 just above the flat plate 28 of the filter paper ascending unit 25.

(3) By lifting the flat plate 28 of the filter paper ascending unit 25 using the air cylinder of the filter paper ascending unit 25 to its full stroke, the filter paper 6 is pushed up to discharge from the filter paper cassette 16 as shown in FIG. 3.

(4) The filter paper which was pushed up by the flat plate 28 at the tip of the air cylinder of the filter paper ascending unit 25 is held by the filter paper holding unit 26 of the filter paper transfer arm 19, and is placed on the filter paper holding seat 31 of the filter paper drier 18.

(5) After the filter paper 6 is placed on the filter paper holding seat 31, the filter paper 6 is detached from the arm of the air cylinder of the filter paper transfer arm 19, and the filter paper holder 7 and the filter paper drier 18 are set as illustrated in FIG. 7 (A).

Drying of Filter Paper

Then, the filter papers are dried.

(1) The switch valves 21a and 21b are opened, the switch valve 11a is closed, and the dehumidified air is passed through the hot air generator 22 to generate hot air. This hot air is then introduced to the filter paper drier 18 from the bottom thereof to dry the filter paper 6 for 30 minutes. Empirically, approximately 5 minutes of drying is sufficient to attain the water content zero state, but 30 minutes are selected for assuring complete drying.

(2) The exhaust air from the filter paper drier 18 passes through the filter paper holder 7 and the dust sampling tube 3 and enters the gas duct 1.

(3) After the completion of the filter paper drying, the switch valve 21b is closed, and the dehumidified cooling air is introduced to the filter paper drier 18 to cool the filter paper 6 for 20 minutes to reach a constant temperature state. Empirically, approximately 10 minutes of dehumidified cooling air introduction is necessary to pass through the filter paper drier 18 to attain a constant temperature state, but 20 minutes are selected for assuring a complete constant temperature state.

(4) As shown in FIG. 7(b), the filter paper drier 18 is lowered by the ascending and descending cylinder 29 of the filter paper drier 18.

Discharge of Filter

The filter paper 6, which thus has been dried and cooled, is transferred onto a filter paper rest plate 35 of the vibration-free balance 20 by the filter paper transfer arm 19. However, the filter paper which was charged with negative electricity when the filter paper passed between the electrodes 61 of the means 60 for discharging electricity is discharged. Thus, the electrically charged filter paper is treated so that a balance error does not arise due to the static electricity when the filter paper is balanced.

Balance of Filter Paper (1) While the filter paper which has been dried and cooled is transferred by the filter paper transfer arm 19, the charged filter paper is discharged between the electrodes 61 of the electricity discharging means 60 and placed on the filter paper rest plate 35.

(2) The filter paper is weighed by the vibration-free balance 20, and then, the filter paper is transferred to the filter paper drier 18 again by the filter paper transfer arm 19. Since the vibration-free balance 20 has an anti-vibratory structure, it assures accurate weighing even if it is installed adjacent to the furnace accompanied with vibration.

Measurement of Dust

The dust measurement steps will now be described below.

(1) The ascending and descending cylinder 29 of the filter paper drier 18 lifts the filter paper drier 18. The filter paper 6 is sandwiched between the filter paper drier 18 and the filter paper holder 7 to be press-joined and to be sealed.

(2) The flow rate of the flue gas flowing in the gas duct 1 is determined by the pitot tube 9, the gas temperature is determined by the thermocouple 8, and the water content is determined by the moisture meter 4.

(3) Using the reversing unit 5, the suction opening of the dust sampling tube 3 is moved to a position facing against the gas flow direction in the gas duct 1.

(4) The switch valve 21$a$ is closed, the switch valves 11$a$ and 11$b$ are opened, and the flue gas is suctioned for sampling.

(5) Based on the data of gas flow rate, gas temperature, and the gas moisture of the flue gas in the gas duct 1, which were obtained in step (2) above, the gas volume suctioned through the dust sampling tube 3 is calculated by means of the flow rate suction unit 10.

(6) The calculated volume of suction gas is introduced by the suction pump 14 from the dust sampling tube 3 while adjusting the opening of the switch valve 11b to assure the uniform suction rate, and the suctioned gas volume is calculated by the gas meter 15.

(7) The gas flowing through the gas duct 1 is suctioned until the collected dust reaches approximately 0.5 mg per 1 cm$^2$ of the filter paper. The suction time is estimated in advance from the existing measured data and the suction time is set in advance.

(8) After completing the suction of the gas, the switch valve 11$a$ is closed, the switch valve 21$a$ is opened, and then the hot air is introduced to perform the drying of the filter paper 6 for 60 minutes. Empirically, approximately 30 minutes of drying is sufficient to attain the zero water content state in the filter paper 6, but 60 minutes are selected for assuring complete drying.

To avoid emission of collected dust with the flow of hot air, the hot air flow rate is limited to 0.1 m/s or less. When a hot plate is used to dry the filter paper 6, however, the emission of collected dust is surely prevented.

(9) Using the reversing unit 5, the suction opening of the dust sampling tube 3 is reversed to face in the same direction as the direction of gas flow in the gas duct 1.

(10) The exhaust hot air from the filter paper drier 18 passes through the filter paper holder 7 and the dust sampling tube 3 and enters the gas duct 1.

(11) The dehumidified cooling air is introduced to the filter paper drier 18 to cool the filter paper 6 for 20 minutes to reach a constant temperature state. Empirically, approximately 10 minutes of dehumidified cooling air introduction is sufficient, but 20 minutes are selected for assuring the complete constant temperature state.

(12) The filter paper drier 18 is lowered by the ascending and descending cylinder 29 of the filter paper drier 18. The dried and cooled filter paper 6 is transferred to the vibration-free balance 20 by means of the filter paper transfer arm 19 to carry out the weight measurement. Before the weight measurement of the filter paper, however, the filter paper which was charged negatively with the electricity is discharged by having the filter paper pass between the electrodes 61 of the electricity discharge means 60 to prevent an error from arising due to the static electricity, out of the results measured by the vibration-free balance.

(13) After the weight measurement of the filter paper 6 is completed by means of the vibration-free balance 20, the filter paper is taken out by the filter paper transfer arm 19.

(14) The dust concentration of the flue gas is calculated from the collected dust weight and the gas volume sucked from the gas duct 1.

Control of the Measurement Processes

All of the cylinders, limit switches, motors, and switch valves used in the above described measurement process are controlled using the input signals generated from the timer and limit switches built in the sequencer. The timer setting is arbitrarily made by entering necessary data through the CPU and the CRT. The program used in the process operated by the means for controlling measurement enables control under complex conditions.

Figure 9:
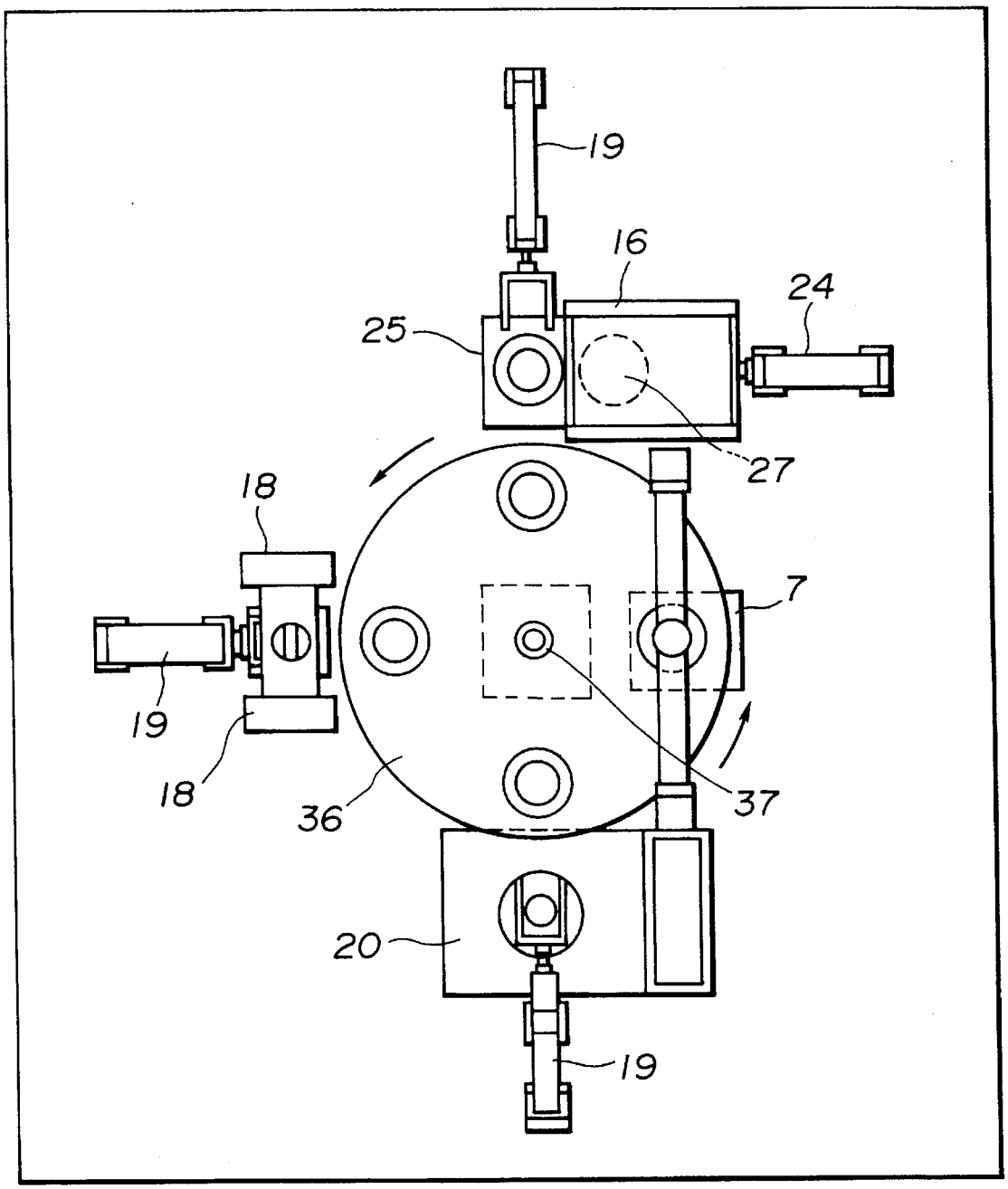
FIG. 9 is another embodiment of the present invention using a turntable.
Figure 10A:
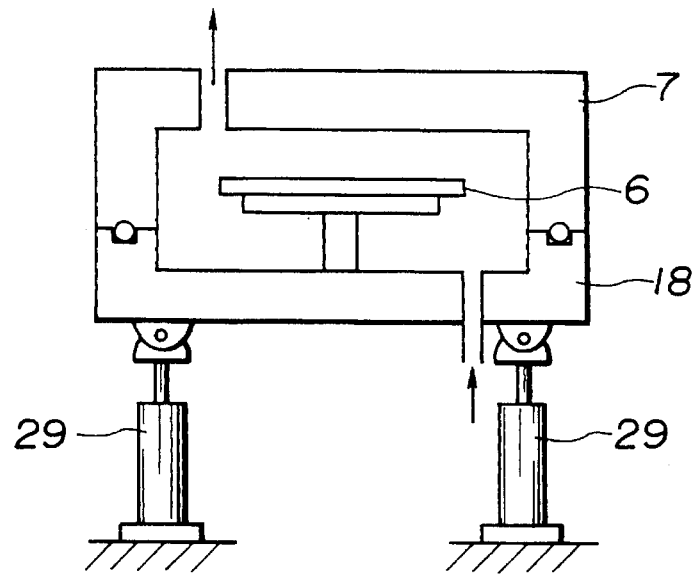
FIG. 10(A) illustrates an instance of drying means being integrated with a cooling means.
Figure 10B:
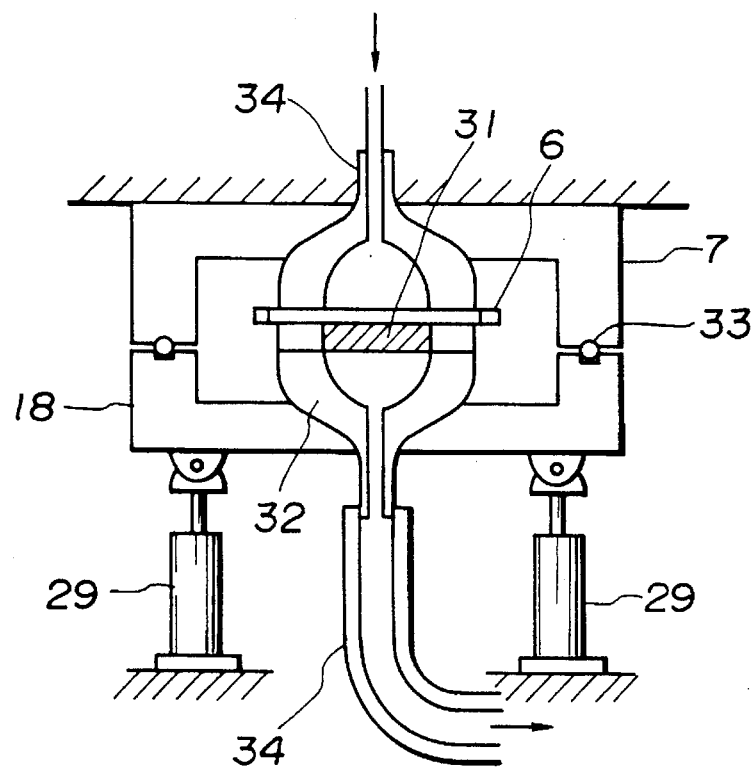
FIG. 10(B) illustrates a separate means for sucking dust according to the present invention.
Figure 11A:
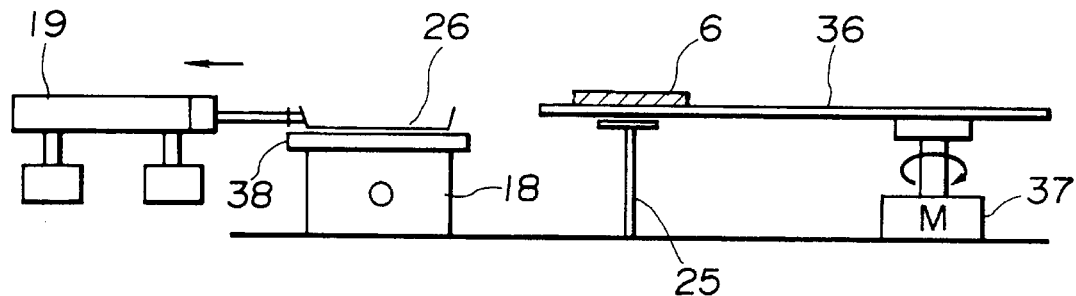
FIGS. 11(A)–11(C) show an embodiment of the present invention which uses a hot plate method.
Figure 11B:
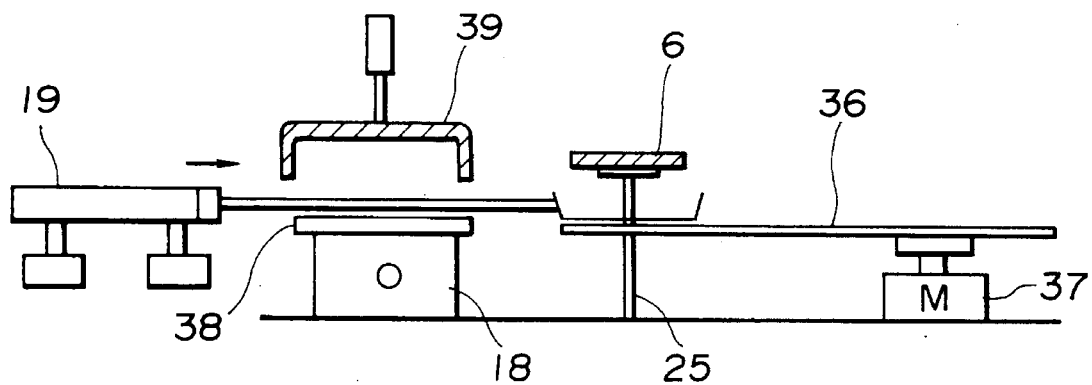
Figure 11C:
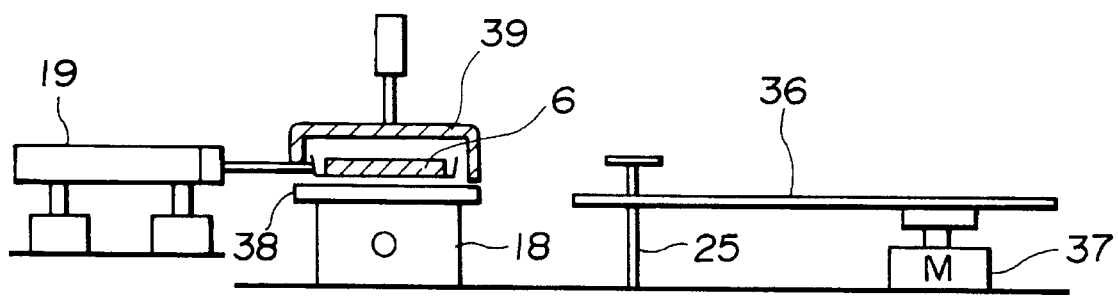

FIG. 9 schematically illustrates a turntable method which is another embodiment of the apparatus for measuring dust concentration according to the present invention. FIG. 10(A) is an illustration of an example of a drying means and a cooling means being integrated. FIG. 10(B) is an illustration of a means for sucking dust. FIGS. 11(A) through 11(C) illustrate another embodiment of the present invention.

In FIG. 9, the turntable 36 is rotatably installed, and the rotary unit 37 rotates the turntable 36.

In the further embodiment of the present invention shown in FIG. 9, a filter paper collecting means, a filter paper drying means, a filter paper weighing means, and a dust sampling means each are given their respective functions on the periphery of the turntable 36. The turntable 36 is rotated freely by the rotary unit 37 to perform individual functions at each of their positions.

Accordingly, the filter paper cassette 16 is pushed out by the air cylinder of the cassette pusher unit 24, then the filter paper is lifted by the filter paper ascending unit 25, and the filter paper 6 is taken out from the filter paper cassette 16 to place the filter paper on the turntable 36. The turntable is rotated by 90 degrees counter-clockwise in the direction of the arrow of FIG. 9.

The filter paper is transferred to place it on the filter paper holding seat 31 of the filter paper drier 18 by the filter paper transfer arm 19, and the filter paper 6 is dried and cooled as in the preceding embodiment. After the completion of drying and constant temperature treatment, the filter paper is placed on the turntable. The turntable 36 is rotated counter-clockwise by 90 degrees to move the filter paper from the filter paper transfer arm 19, and the filter paper 6 is weighed on the balance 20 in the filter paper feeding and weighing means. After the filter paper is weighed, the turntable 36 is rotated counter-clockwise by 90 degrees to the point of the filter paper holder 7 in the dust sampling means, where the flue gas is introduced to sample the dust on the filter paper 6. The measurement of the introduced gas volume and other processes are the same as those of the preceding embodiment.

After completing the sampling, the turntable 36 is rotated clockwise by 180 degrees, and the filter paper is placed on the filter paper holding seat 31 on the filter paper dryer 18 to dry the filter paper 6 and to bring the filter paper to a constant temperature state. Then, the turntable 36 is rotated to weigh the filter paper at the filter paper feeding and weighing means and to determine the dust concentration.

FIGS. 10(A) and 10(B) illustrate states of the turntable method shown in FIG. 9, where FIG. 10(A) shows an integrated drying and cooling means, and FIG. 10(B) shows a separated unit of the dust sampling means.

If, as shown in FIG. 10(A), the drying means and the cooling means are integrated at one position of the filter paper drying means of the turntable in FIG. 9, and if the dust sampling means in FIG. 10(B) is positioned at the dust sampling means of the turntable, then there is provided a further merit to treat more than one sample on the turntable at a time.

FIGS. 11(A)–11(C) show a still further embodiment of the present invention for drying the filter paper with a hot plate method. FIGS. 11(A)–11(C) show the turntable 36, the rotary unit 37, the hot plate 38, and the hot plate lid 39.

As illustrated in FIG. 11(A), the filter paper 6 on the turntable 36 is lifted by the filter paper ascending unit 25. Then, as illustrated in FIG. 11(B), the filter paper holding unit 26 is extended to the point above the filter paper ascending unit 25 to the full stroke of the air cylinder. Finally, as illustrated in FIG. 11(C), the filter paper 6 is placed on the hot plate 38 on the filter paper drier 18 which is then sealed with the hot plate lid 39 to implement the drying process. After completing the drying, the filter paper is transferred by the steps reverse to those of the preparation.

Furthermore, the hot plate type hot air drier 18 comprises the hot plate 38 which raises and lowers, and the hot plate lid 39. Since the hot plate 38 has a limited capacity to store only one sheet of filter paper, the size of the hot plate 38 is minimized.

There is another method of cooling to bring the filter paper to a constant temperature. Instead of using cooling air, the filter paper 6 is transferred onto the vibration-free balance 20 immediately after drying by the filter paper transfer arm 19 to apply air cooling. Even under air cooling, the filter paper reaches a constant temperature within two to three minutes and gives very little error in the weight measurement of the filter paper 6. Nevertheless, the holding time is prolonged to assure the result.

The embodiment of the present invention deals with the case where the dust concentration in the flue gas is determined in every sample. However, normally three or more samples are needed to be measured so as to assure an accurate analysis. In that case, the turntable method described above is applicable to shorten the measuring process by conducting the drying of the filter paper 6 and the suction of gas in the gas duct 1 simultaneously. Accordingly, the turntable method is a preferable method.

Figure 12:
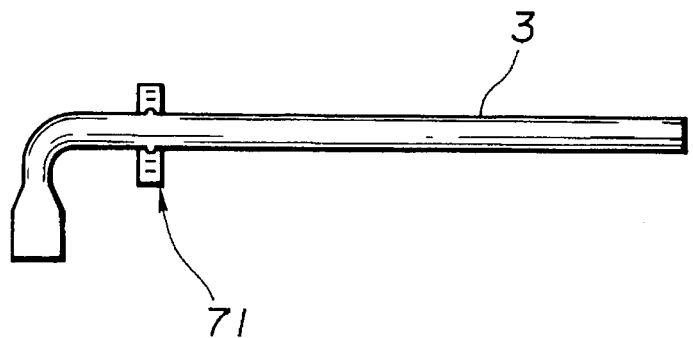
FIG. 12(A) shows a dust sampling tube according to the present invention.
FIGS. 12(B) and 12(C) shows the dust sampling tube with projections thereon.
FIG. 12(D) shows a vibration ring in detail according to the present invention.
Figure 12:
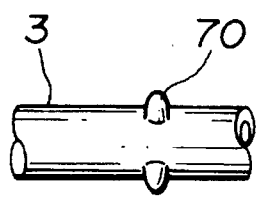
Figure 12:
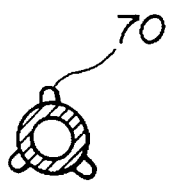
Figure 12:
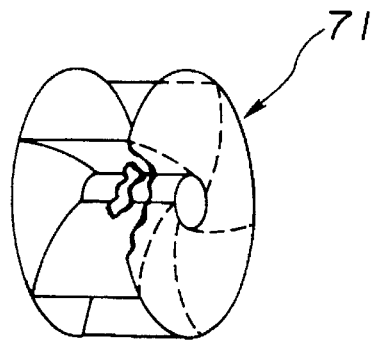
Figure 13:
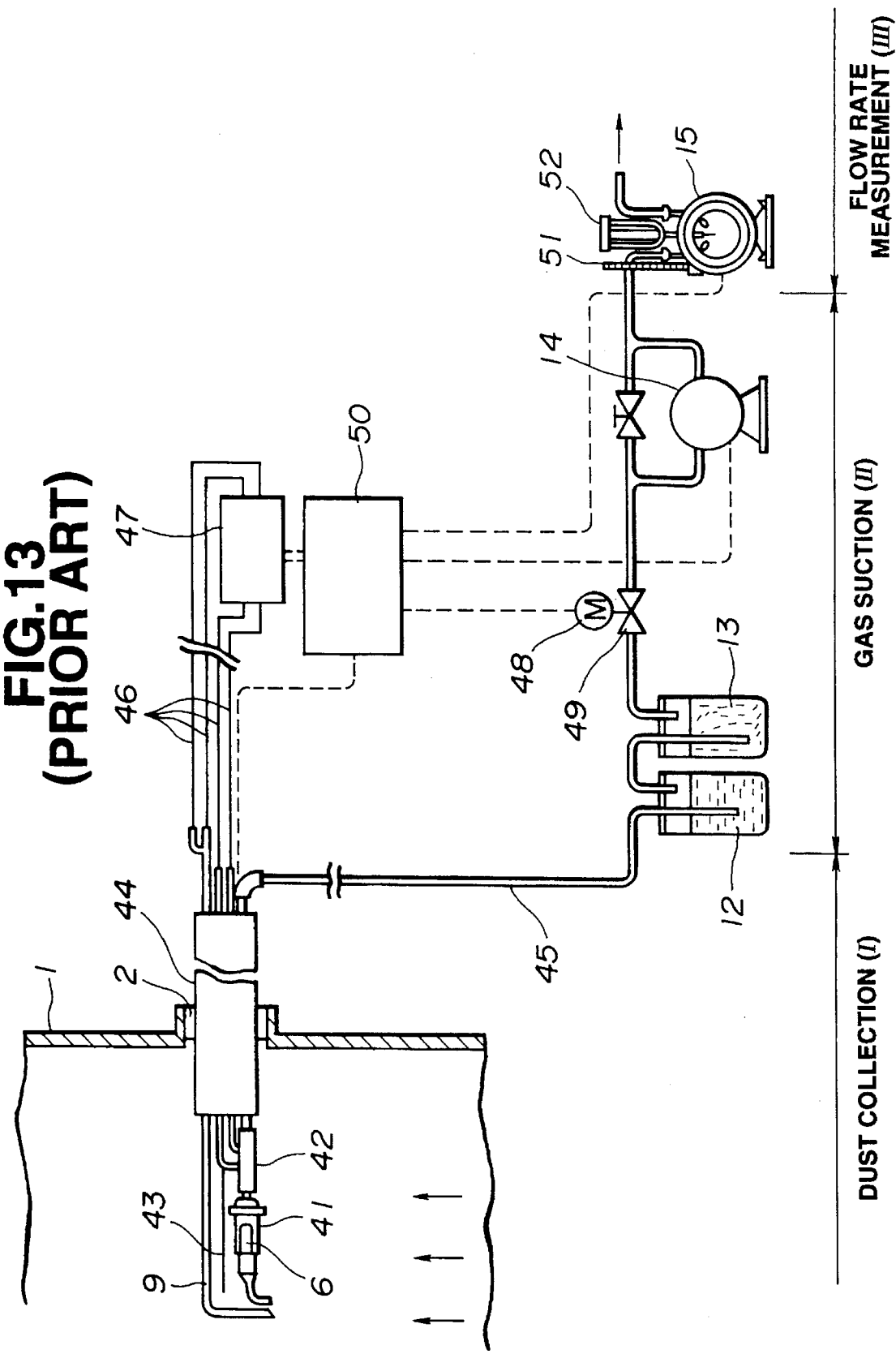
FIG. 13 illustrates a prior art apparatus for automatically measuring dust concentration in flue gas which conforms to JIS Z-8808.
Figure 14:
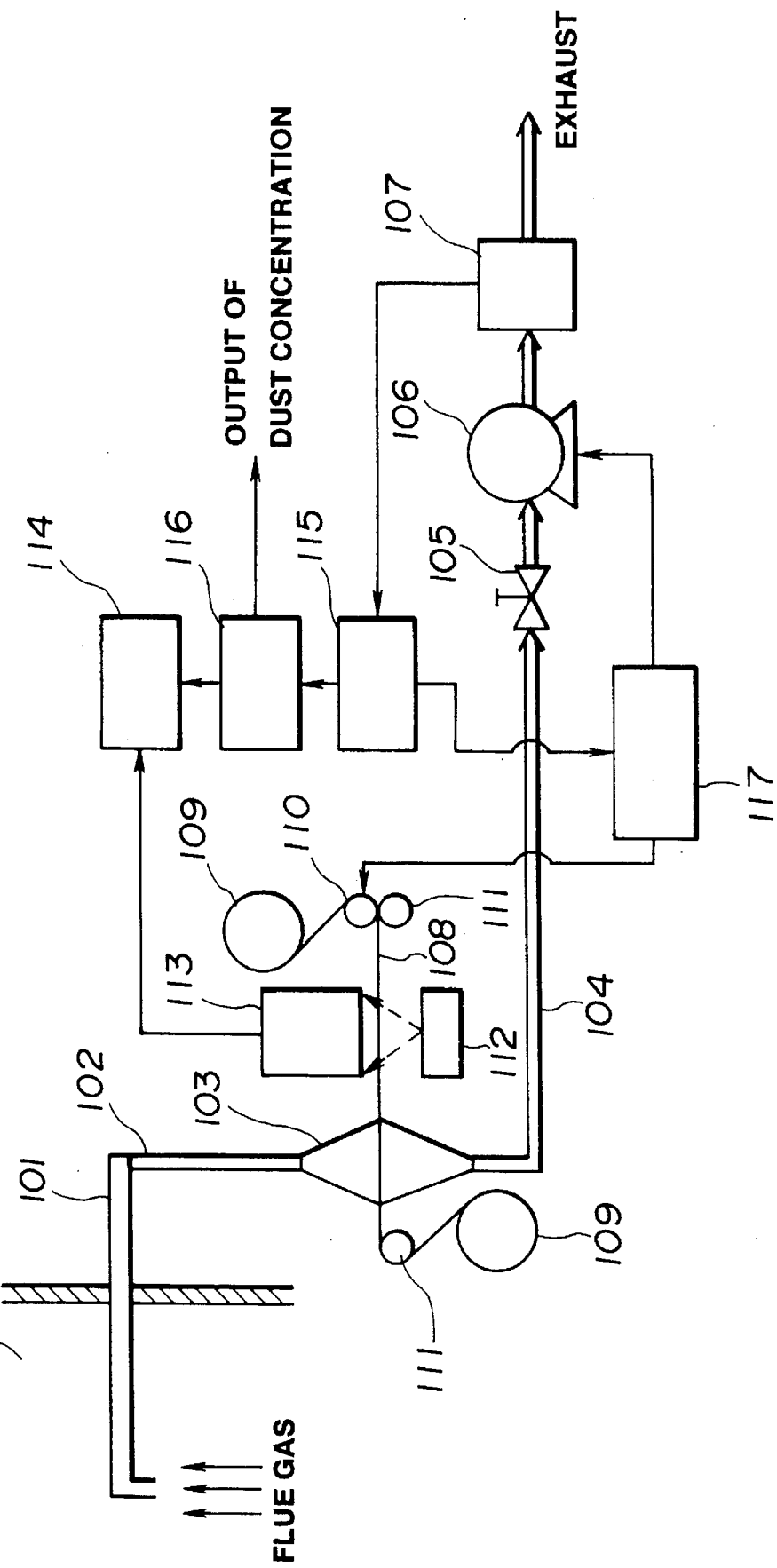
FIG. 14 illustrates another prior art apparatus for automatically measuring dust concentration in flue gas according to the β ray method.

When, as shown in FIG. 12(A), the flue gas sucked through a suction opening provides laminar flow in the dust sampling tube 3, the gas flow rate is zero. In this case, on the way to introducing dust to the filter paper, the dust adheres to the inner wall of the dust sampling tube and the dust sampling tube is closed with the adhesion dust. To avoid this closing as a result of gas adhesion, the gas flow in the sampling tube is made to form a turbulent flow by making the inner section area of the dust sampling tube with a small radius and a Reynolds number of 2000 or more.

Further, as shown in FIGS. 12(B) and 12(C), projections 70 are placed on a predetermined location of a periphery of the dust sampling tube and as shown in FIG. 12(D), a rotary vibration ring 71 is placed in the sampling tube to prevent the dust from adhering to the inner wall of the dust sampling tube.

An operating procedure of the above embodiment of the present invention will be described below.

(1) The units for the measurement are prepared. The filter paper cassettes 16 are taken out one by one from the filter paper stocker 17. Each of the filter paper cassettes 16 is mounted on the hot air filter paper drier 18.

(2) Hot air is introduced from the hot air generator 22 to conduct drying of the filter paper for approximately 30 minutes to remove all the water content from the filter paper.

(3) The switch valve 21a on the hot air generator 22 is switched to cool the filter paper by means of a dehumidified cooling air until the filter paper reaches a constant temperature.

(4) The filter paper is transferred to the vibration-free balance 20 by means of the filter paper transfer arm 19 to weigh the filter paper.

(5) The temperature of the flue gas in the gas duct 1 is determined by the thermocouple 8, the water content of the gas is determined by the moisture meter 4, and the gas flow rate of the gas is determined by the pitot tube 9.

(6) The gas sampling tube 3 inserted into the measurement hole on the gas duct 1 sucks the flue gas by the flow rate suction unit 10 at the same flow rate as that of the flue gas in the gas duct measured by the pitot tube 9.

(7) The flue gas is sucked until the collected dust reaches approximately 0.5 mg per 1 $cm^2$ of the filter paper. The suction time is determined in advance from the existing measured data and the suction time is set in advance.

(8) The filter paper 6 is transferred to the hot air filter paper drier 18, where the filter paper is dried at a temperature range of from 105° to 110° for about 1 hour to perfectly remove the water.

(9) Using the dehumidified air, the filter paper is cooled approximately 20 minutes to reach a constant temperature.

(10) The filter paper is transferred to the vibration-free balance 20 by means of the filter paper transfer arm 19 to weigh the filter paper.

(11) The dust concentration of the flue gas is calculated from the weight of the collected dust and the volume of gas sucked from the gas duct 1.

(12) To stop the measurement, the sampling opening is reversed by the reversing unit 5 of the sampling tube 3 to avoid any accumulation of dust at the sampling opening.

Table 1 shows the process of the measurement for continuous three samplings repeating the steps (2) through (11).

As clearly shown in Table 1, the time required for the dust concentration measurement in flue gas is shortened from 18 hours in the prior art to 8 hours in the present invention. In addition, the centralized control is applicable during the measuring process with improved accuracy.

Furthermore, Table 2 shows the results of the measurement on the conditions that (1) the inner diameter of the sampling tube is 4 mm so that the flow rate of the gas flue which has been sucked through the dust sampling tube 3 with the inner diameter of 6 mm is 8 to 15 m/sec. by means of the equal flow rate suction when the flow rate of the gas flue which is to be measured is 4 to 7 m/sec, and that (2) the vibration ring 70 is also placed in the dust sampling tube 3.

As clearly seen in Table 2, the adhesion of the dust to the filter paper is suppressed in a range which is extremely small.

The electrified filter paper is discharged by having the electrified filter paper pass between the electrodes 61 of the means for discharging the electricity 60 which is connected to the direct current power source of 100 V. Thus, any error in measurement arising as a result of static electricity, is avoided. As clearly seen in Table 3, any error is extremely small.

According to the concentration apparatus of the present invention, the following effects are obtained.

(1) The use of a vibration-free balance allows the precise weight measurement under vibratory conditions and allows precise dust concentration measurement.

(2) The use of a hot air filter paper drier and a moisture meter eliminates excess drying time and provides a prompt measurement.

(3) The application of negative pressure in the sampling tube during non-sampling times by means of the reversing unit prevents the dust from adhering to the sampling tube, and the elimination of the residual dust from the sampling tube allows an accurate measurement.

(4) The use of the filter paper cassette, the filter paper transfer arm, and the hot air filter paper drier, which are exclusive for the filter paper, allows a compact design of the apparatus and allows an easy transfer of the apparatus in the case that a single apparatus is used for the dust concentration measurement at more than one point.

(5) Since the means for discharging the electricity is installed, good results in the measurement with an extremely small error is obtained even if the dust is collected from the gas duct by means of the dust collector placed on the duct.

(6) The precise measurement of data is obtained by having the gas flue flow in the form of turbulent flow and vibrating the sampling tube which prevents the dust from adhering to the inner wall of the sampling tube.

TABLE 1

| Work item | Work time | | | | | | | |
|---|---|---|---|---|---|---|---|---|
| | 1 | 2 | 3 | 4 | 5 | 6 | 7 | 8 |
| | 20 40 60 | 20 40 60 | 20 40 60 | 20 40 60 | 20 40 60 | 20 40 60 | 20 40 60 | 20 40 60 |
| 1. Setting apparatus | 60' | | | | | | | |
| 2. Drying filter paper | | 30' | 30' | 30' | | | | |
| 3. Bringing filter paper to constant weight | | 20' | 20' | 20' | | | | |
| 4. Weighing filter paper | | 5' | 5' | 5' | | | | |
| 5. Measurement of flue gas composition | | | | 5' | | | | |
| 6. Calculation of uniform suction rate | | | 5' | 5' | 5' | | | |
| 7. Dust sampling (1) | | | 60' | | | | | |
| 8. Dust sampling (2) | | | | 60' | | | | |
| 9. Dust sampling (3) | | | | | 60' | | | |
| 10. Drying filter paper | | | | | 60' | 60' | 60' | |
| 11. Bringing filter paper to constant weight | | | | | 20' | 20' | 20' | |
| 12. Weighing filter paper | | | | | 5' | 5' | 5' | |
| 13. Calculation of dust concentration | | | | | | 5' | 5' | |
| 14. Transfer of apparatus | | | | | | | | 60' |

TABLE 2

| Kind of Fuel | | (A) Total Amount of Collected Dust (mg) | (B) Dust Adhesion to Sampling Tube | | | |
|---|---|---|---|---|---|---|
| | | | Prior Art | | Invention | |
| | | | Amount (mg) | Ratio (%) | Amount (mg) | Ratio (%) |
| Heavy Oil | 1 | 35.5 | 3.0 | 8.5 | 1.2 | 3.4 |
| Class A | 2 | 36.0 | 2.3 | 6.4 | 1.8 | 5.0 |
| | 3 | 45.2 | 3.5 | 7.7 | 2.2 | 4.9 |
| | 4 | 26.0 | 2.3 | 9.0 | 0.7 | 2.7 |
| | 5 | 18.5 | 2.7 | 14.5 | 0.4 | 2.2 |
| | Average | 32.2 | 2.8 | 9.2 | 1.3 | 3.6 |
| Coke Oven | 1 | 1.3 | 0.2 | 15.4 | 0.06 | 4.6 |
| Gas | 2 | 1.5 | 0.2 | 13.3 | 0.05 | 3.3 |
| | 3 | 1.4 | 0.4 | 28.6 | 0.04 | 2.9 |
| | 4 | 2.0 | 0.4 | 20.0 | 0.06 | 3.0 |
| | 5 | 1.8 | 0.3 | 16.7 | 0.06 | 4.4 |
| | Average | 1.6 | 0.3 | 18.8 | 0.06 | 3.7 |
| Combustibles | 1 | 6.4 | 1.4 | 22.4 | 0.20 | 3.1 |
| (from an | 2 | 5.7 | 1.8 | 32.2 | 0.14 | 2.5 |
| Incinerator) | 3 | 6.1 | 0.9 | 15.4 | 0.09 | 1.5 |
| | 4 | 7.5 | 1.4 | 18.4 | 0.17 | 2.3 |
| | 5 | 9.4 | 1.4 | 15.0 | 0.42 | 4.5 |
| | Average | 7.0 | 1.4 | 20.7 | 0.20 | 2.8 |

Note: Ratio in the item column is caluculated by the formula of $\{(B)/(A)\} \times 100$

TABLE 3

| | | | | | | | | | | | | Unit:mg | |
|---|---|---|---|---|---|---|---|---|---|---|---|---|---|
| No. of Measurement | | 1 | 2 | 3 | 4 | 5 | 6 | 7 | 8 | 9 | 10 | Average | Error Ratio (%) |
| True Value | | 6.4 | 5.7 | 6.1 | 7.5 | 9.4 | 4.8 | 5.6 | 6.4 | 7.2 | 6.6 | 6.6 | — |
| Without Electricity Discharge | | 8.3 | 7.3 | 7.4 | 10.0 | 12.0 | 6.5 | 7.3 | 8.0 | 9.6 | 8.2 | 8.5 | 28.8 |
| With Electricity Discharge | | 6.3 | 5.7 | 6.0 | 7.5 | 9.3 | 4.8 | 5.7 | 6.4 | 7.2 | 6.6 | 6.6 | 0 |

What is claimed is:

1. An apparatus for automatically measuring dust concentration in flue gas travelling in a gas duct, comprising:
   (a) sampling means for sampling dust in flue gas;
   (b) measuring means for measuring a volumetric gas flow rate of the flue gas;
   (c) feeding and weighing means for feeding and weighing a filter paper for filtering the sampled gas, said feeding and weighing means comprising:
      (i) a filter paper cassette for storing the filter paper,
      (ii) a filter paper stocker for storing a plurality of the filter paper cassettes,
      (iii) a cassette pusher unit for pushing a filter paper cassette out of the filter paper stocker,
      (iv) a filter paper ascending unit for raising the filter paper,
      (v) a filter paper drier for drying the filter paper,
      (vi) a filter paper transfer arm for transferring the filter paper between the filter paper cassette, the filter paper ascending unit and the filter paper drier,
      (vii) a vibration-free balance for balancing the filter paper, and
      (viii) a hot air generation unit; and
   (d) controlling means for transmitting data among said dust sampling means, said measuring means, and said feeding and weighing means, and for controlling a sequence of operations thereof.

2. The apparatus of claim 1, wherein said sampling means comprises a dust sampling tube with a suction opening for sucking the flue gas through the suction opening, and a reversing unit which rotates the dust sampling tube so that the suction opening is facing in an opposite direction corresponding to a reverse direction of flue gas flow.

3. The apparatus of claim 2, wherein the sampling tube has a sectional area and the Reynolds number in said sampling tube is 2000 or more.

4. The apparatus of claim 2, wherein the sampling tube has a vibrator for vibrating the sampling tube, said vibrator including at least one projection placed on a periphery of the sampling tube and a rotatable vibration ring placed over the at least one projection.

5. The apparatus of claim 1, wherein said measuring means comprises a thermocouple for measuring temperature of the flue gas, a moisture meter for measuring water content in the flue gas, a pitot tube for measuring gas flow rate when the flue gas is sampled, a suction unit for sucking the sampled flue gas at a flow rate which is the same as the flow rate of the flue gas travelling in the gas duct, a gas suction pump, and a gas meter for measuring the sucked flue gas.

6. The apparatus of claim 1, wherein said controlling means comprises a sequencer and a central processing unit, said sequencer controlling transmission of gas characteristics between said sampling means and said measuring means, and controlling transfer of the filter paper and weighing of the filter paper by means of electric signals.

7. The apparatus of claim 1, wherein the filter paper drier includes a hot plate and a lid covering the hot plate, the lid being ascendable and descendable.

8. The apparatus of claim 1, further comprising a means for discharging electricity of the dust which has been electrically charged.

9. An apparatus for automatically measuring dust concentration in flue gas travelling in a gas duct, comprising:

(a) sampling means for sampling dust in flue gas;

(b) measuring means for measuring a volumetric gas flow rate of the flue gas;

(c) feeding and weighing means for feeding and weighing a filter paper for filtering the sampled gas, said feeding and weighing means comprising:

(i) a filter paper cassette for storing the filter paper, (ii) a filter paper stocker for storing a plurality of the filter paper cassettes, (iii) a cassette pusher unit for pushing a filter paper cassette out of the filter paper stocker, (iv) a filter paper ascending unit for raising the filter paper, (v) a filter paper drier for drying the filter paper, (vi) a filter paper transfer arm for transferring the filter paper between the filter paper cassette, the filter paper ascending unit and the filter paper drier, (vii) a vibration-free balance for balancing the filter paper, and (viii) a hot air generation unit;

(d) controlling means for transmitting data among said dust sampling means, said measuring means, and said feeding and weighing means, and for controlling a sequence of operations thereof; and (e) said filter paper cassette, cassette filter paper pusher unit, filter paper ascending unit, filter paper drier, filter paper transfer arm, and vibration-free balance being located in a periphery of a rotatable turntable.

10. The apparatus of claim 9, wherein said sampling means comprises a dust sampling tube with a suction opening for sucking the flue gas through the suction opening, and a reversing unit which rotates the dust sampling tube so that the suction opening is facing in an opposite direction corresponding to a reverse direction of flue gas flow.

11. The apparatus of claim 10, wherein the sampling tube has a sectional area and the Reynolds number in said sampling tube is 2000 or more.

12. The apparatus of claim 10, wherein the sampling tube has a vibrator for vibrating the sampling tube, said vibrator including at least one protection placed on a periphery of the sampling tube and a rotatable vibration ring placed over the at least one projection.

13. The apparatus of claim 9, wherein said measuring means comprises a thermocouple for measuring temperature of the flue gas, a moisture meter for measuring water content in the flue gas, a pitot tube for measuring gas flow rate when the flue gas is sampled, a suction unit for sucking the sampled flue gas at a flow rate which is the same as the flow rate of the flue gas travelling in the gas duct, a gas suction pump, and a gas meter for measuring the sucked flue gas.

14. The apparatus of claim 9, wherein said controlling means comprises a sequencer and a central processing unit, said sequencer controlling transmission of gas characteristics between said sampling means and said measuring means, and controlling transfer of the filter paper and weighing of the filter paper by means of electric signals.

15. The apparatus of claim 9, wherein the filter paper driver includes a hot plate and a lid covering the hot plate, said lid being acendable and descendable.

\* \* \* \* \*